United States Patent [19]

Waitz et al.

[11] Patent Number: 5,484,417
[45] Date of Patent: Jan. 16, 1996

[54] MICROCANNULA

[75] Inventors: Harold D. Waitz; Hal Sternberg; Paul E. Segall, all of Berkeley; Bruce Cohen, Richmond, all of Calif.

[73] Assignee: BioTime, Inc., Berkeley, Calif.

[21] Appl. No.: 348,743

[22] Filed: Nov. 30, 1994

Related U.S. Application Data

[63] Continuation of Ser. No. 237,826, May 4, 1994, abandoned, which is a continuation of Ser. No. 25,158, Mar. 1, 1993, abandoned, which is a continuation-in-part of Ser. No. 687,843, Apr. 19, 1991, abandoned.

[51] Int. Cl.$^6$ .................................................. A61M 5/178
[52] U.S. Cl. ........................ 604/165; 604/264; 604/239; 604/274
[58] Field of Search .................................... 604/264, 265, 604/164–168, 158, 239, 280, 272–274; 606/223

[56] References Cited

U.S. PATENT DOCUMENTS

| | | | |
|---|---|---|---|
| 3,750,667 | 8/1973 | Pshenichny | 604/165 |
| 3,788,119 | 1/1974 | Arrigo | 604/265 |
| 4,191,176 | 3/1980 | Spina | 604/274 |
| 4,411,657 | 10/1983 | Galindo | 604/274 |
| 4,413,993 | 11/1983 | Guttman | 604/274 |
| 4,588,398 | 5/1986 | Dougherty | 604/265 |
| 4,808,170 | 2/1989 | Thornton | 604/274 |
| 4,842,585 | 6/1989 | Witt | 604/158 |
| 4,994,036 | 2/1991 | Biscoping | 604/158 |
| 5,100,390 | 3/1992 | Lubeck | 604/158 |

OTHER PUBLICATIONS

American Heritage Dictionary, second edition, 1982 p. 257.

*Primary Examiner*—C. Fred Rosenbaum
*Assistant Examiner*—Chalin Smith
*Attorney, Agent, or Firm*—Fish & Richardson; Karl Bozicevic; Valeta Gregg

[57] ABSTRACT

The invention is a microcannula which comprises a hollow tube having a small cross sectional size and a side beveled tip wherein the angle of the bevel is about 25 degrees. A segment of the hollow tube distal to the beveled tip has an expanded outside diameter which may be provided by a tightly fitting ring member which may be moved to a desired position on the outside of the hollow tube. The tight fit of the ring is preferably obtained through an interference fit between the ring and the out side surface of the hollow tube. A conically tiped trochar is fitted tightly but removably in the lumen of the hollow tube. The trochar may be provided with a flattened or swedged segment.

17 Claims, 3 Drawing Sheets

TOP

SIDE

MICROCANNULA

This is a continuation of application Ser. No. 08/237,826, filed May 4, 1994, now abandoned, which is a continuation of Ser. No. 08/025,158, filed Mar. 1, 1993, now abandoned, which is a continuation-in-part application of U.S. patent application Ser. No. 07/687,843 filed Apr. 19, 1991, now abandoned.

FIELD OF THE INVENTION

The present invention relates to the field of surgical devices.

BACKGROUND OF THE INVENTION

Cannulas are hollow tube instruments used to deliver fluids or remove fluids from blood vessels, ducts or other hollow organs of animals. While many sizes of cannulas are available commercially, microcannulas suitable for use in surgery on small animals are of limited design and utility, The smallest available cannulas are generally flat tipped and are large enough to accommodate a 14 to 24 gauge needle in the lumen of the cannula, which needle is used as a trochar. Small cannulas are generally made of small bore polyethylene or PTFE tubing and are supplied with a hypodermic needle which is used to block a cannula to prevent fluid contained in the vessel of the hollow organ from draining until the cannula is in place in a pre-made incision in the vessel or other hollow organ.

As cannulas decrease in size, they are more flexible and easily bent and therefor difficult to manipulate. The flexibility of small cannulas occurs because of the decreasing absolute wall thickness of the cannula as they get smaller in diameter, and concomitant loss of rigidity of the cannula wall.

Conventional cannulas are supplied with trochars that move freely in the lumen of the cannula since it is conventionally desirable to be able to quickly remove the trochar once a vessel is cannulated.

Conventional small cannulas appropriate for use in cannulation of small blood vessels in microsurgery are notoriously difficult to use. The smallest cannulas available frequently require many minutes of patient and skilled manipulation to prepare a micro-incision in a blood vessel and properly place the cannula in small blood vessels. Furthermore such small cannulas suitable for microsurgery are frequently supported by an outside surrounding heavy gauge needle or auxiliary tube and the microcannula is placed inside the supporting tube. One of the main disadvantages of this conventional arrangement of microcannula and surrounding-supporting tube is that the wound made by the larger supporting hollow tube is larger than that which would be required if the microcannula were more robust.

SUMMARY AND OBJECTS OF THE INVENTION

The present invention comprises a very small bore cannula having a beveled tip with a sharp pointed trochar tightly, but removably placed in the lumen of the cannula. This cannula or microcannula and associated trochar have sufficient rigidity to be relatively easily manipulated. Furthermore by means of using a sharp pointed trochar and bevel tipped cannula, it is possible to cannulate a small blood vessel with out the necessity of incising the blood vessel wall before inserting the cannula and trochar. The microcannula according to the invention is also provided with a segment having an expanded outer diameter, this expanded segment distal to the beveled tip of the microcannula is useful for securing the cannula in the cannulated blood vessel or other hollow anatomical structure, as is described herein below.

It is an object of the invention to provide an easily manipulated cannula which can be used to cannulate small hollow organs and blood vessels in a short period of time.

It is another object of the invention to provide a microcannula and trochar that function together as a unit to provide rapid cannulation with a minimum of blood loss.

It is yet another object of the invention to provide a microcannula and trochar that can be used to cannulate a blood vessel without making a preparatory incision before inserting the trochar and cannula into the blood vessel.

It is still another object of the invention to provide a microcannula that can be easily secured in the cannulated blood vessel or other hollow anatomical structure.

DETAILED DESCRIPTION OF THE INVENTION

In greater detail, the microcannula according to the invention comprises a hollow tube 12 having a cross sectional size smaller that a 24 gauge needle and larger than a 29 gauge needle. More precisely the outside diameter of said tube which comprises the body of the microcannula is about 0.016 inch. The outside diameter of the tubing will vary slightly but in general the outside diameter of the tube will be between 0.018 and 0.014 inch. Usually the outside diameter of the tubing will be 0.016"+/−0.001 inch.

The inside diameter of the tube which comprises the body of the microcannula is about 0.008 inch. The inside diameter of the tubing will vary slightly but in general the inside diameter of the tube will be on a range between 0.010 and 0.006 inch. Usually the inside diameter of the tubing will be 0.008+/−0.001 inch.

Figure 2:
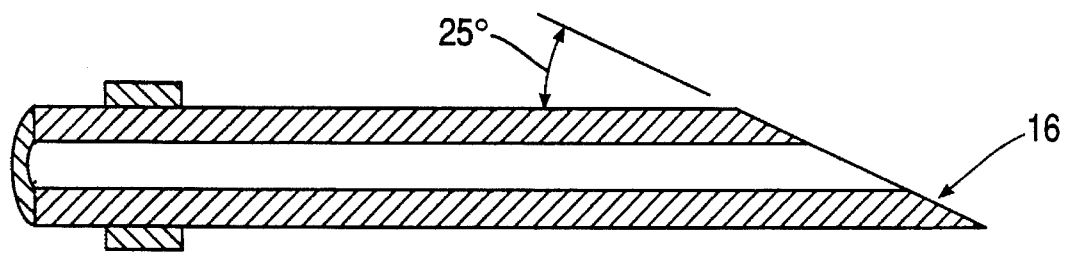
FIG. 2 is a cross-section of the microcannula according to the invention.
Figure 3:
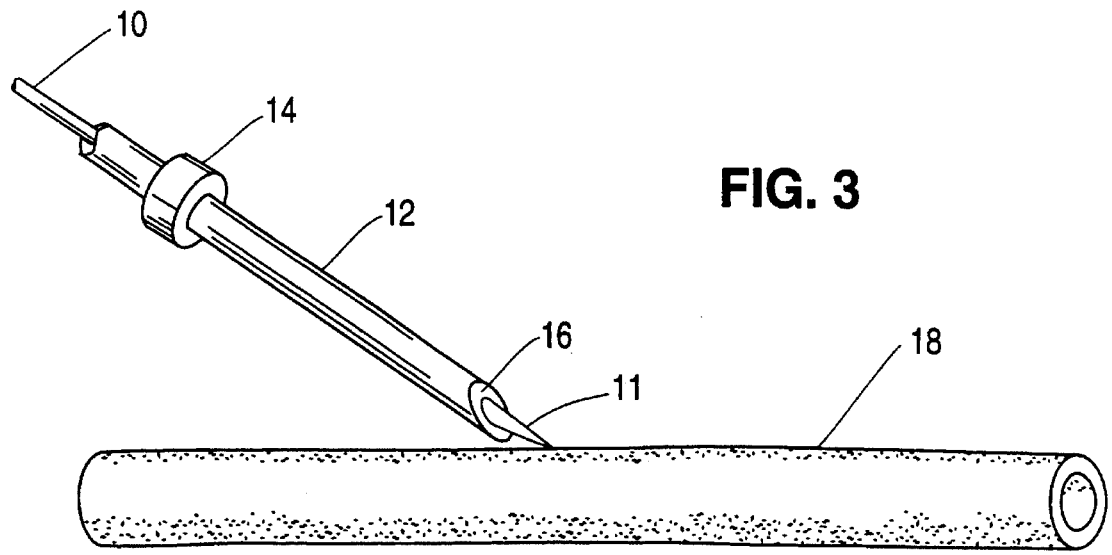
FIG. 3 shows the trochar and microcannula in use as a unit just prior to penetration of a blood vessel wall or other hollow tube by the point of the trochar.
Figure 4:
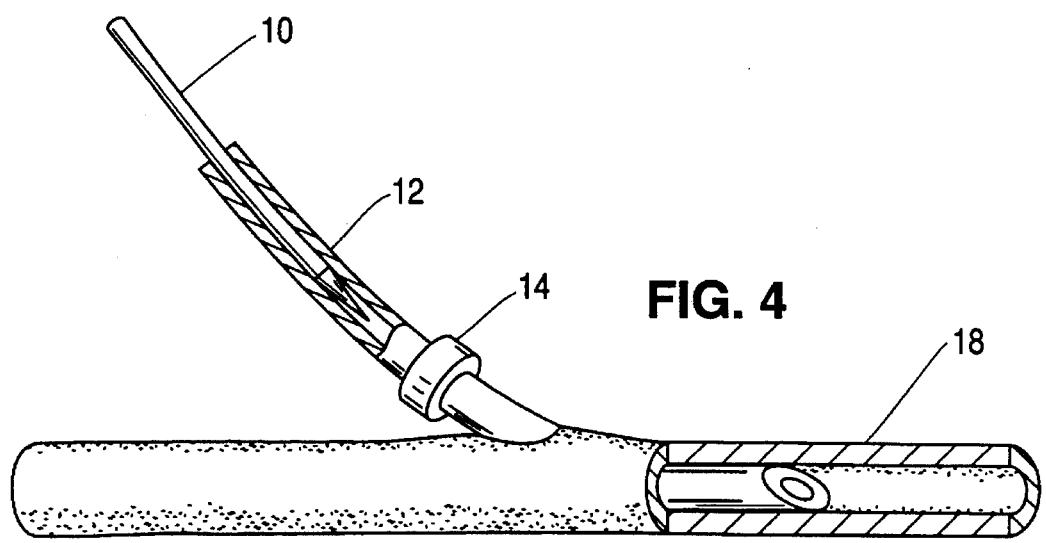
FIG. 4 shows the microcannula in place in a blood vessel or other hollow tube with the trochar in the process of being with drawn.

The microcannula according to the invention will have a simple beveled tip. The angle of said bevel is about 25°. The angle of the bevel may vary in a range between 23 and 27 degrees, but the best performance of the microcannula is achieved when the bevel is 25°+/−0.5°. The angle of the microcannula tip mentioned herein above is measured with respect to one side of the microcannula tube as is shown in FIG. 2.

The microcannula of the invention will generally be made of bio-compatible polymer tubing. It is preferred that the bio-compatible polymer be perfluorocarbon material.

The microcannula described above is highly flexible and delicate and is difficult to insert into the lumen of a blood vessel 18 or other hollow organ requiring cannulation. In order to facilitate manipulation of the microcannula, a trochar 10 is provided for use with the microcannula. The trochar fits in the lumen of the microcannula tube and may be removed therefrom. It is preferred that the trochar be of a size that fits tightly in the lumen of the microcannula tube and does not move freely in the lumen; however, the trochar must also be small enough to be removed from the lumen of the microcannula when the side of the microcannula is grasped and held and the trochar is pushed or pulled from the lumen of the tube. The preferred performance of the trochar is best obtained when the outside diameter of the trochar is slightly smaller than the inside diameter of the tube.

Figure 6:
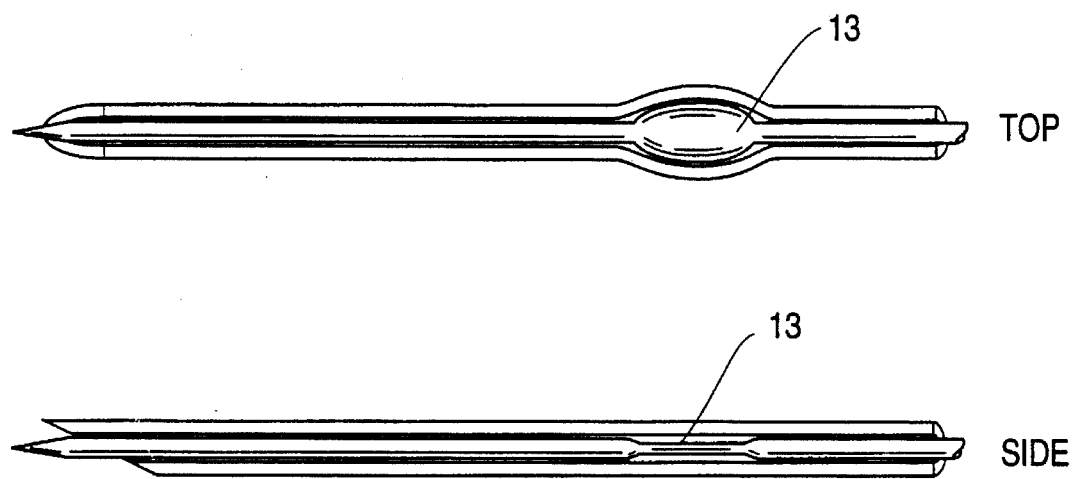
FIG. 6 shows top and side views of the trochar shown in FIG. 1 with the flattened segment distal to the pointed tip of the trochar which provides contact with the inner walls of the lumen of the microcannula.

In a preferred embodiment, a portion of the length of the trochar will be expanded in width to provide contact with the inner walls of the lumen of the microcannula. This contact provides friction with the inner wall of the microcannula. This friction holds the trochar in the microcannula tube when the tip of the trochar and microcannula contact, pierce and advance into blood vessel or other hollow anatomical structure to be cannulated. In a preferred embodiment the expanded in width portion of the length of the trochar will be provide by a flattened or swedged segment (13) of the trochar which is wider than the average diameter of the wire from which the trochar is formed (FIG. 6).

The flattened or swedged segment of the trochar is generally found distal to the pointed tip of the trochar, wherein the distal direction is the direction away from the tip of the trochar. While the flattened or swedged segment is located at any point distal to the tip of the trochar and may be provided at any point on the length of the trochar, it is preferred to limit the flattened or swedged portion to a segment which fits into the distal end of the microcannula when the trochar is inserted within the lumen of the microcannula with the tip of the trochar extending beyond the tip of the microcannula.

Although it is possible to provide a wire that has a spline or edge or is extruded in an oval cross section, wherein the spline, edge of portion of the oval cross-section wire would contact the inside of the wall of the tube forming the microcannula, it is preferred that the length of the swedged or flattened segment is only a small portion of the length of the trochar. For microcannulas according to the invention it is preferred that the swedged portion not exceed 5 mm in length. In general the swedged portion will not be shorter than the diameter of the wire from which the trochar is formed. Preferably, the length of the swedged portion will be 1.25 to 4 times the diameter of the wire from which the trochar is formed.

In more detail, and as a non-limiting example of a preferred embodiment, the trochar is formed of a substantially round wire having a diameter of 0.008". The swedged segment will consist of a flattened area which is about 0.016" wide in its widest dimension measured perpendicular to axis of the length of the wire and about 0.024" in length measured with the axis of the length of the wire. In general, if the round wire has an average diameter 0.008", the width of the swedged segment will be in a range between 0.019" and 0.015".

The swedged segment resulting from the flattening process which is described herein below, will generally be thinner than the average diameter of the wire when measured in the plane perpendicular to the widest dimension of the swedged segment. Thus, for example in a preferred embodiment, the thickness of the swedged segment of an average diameter 0.008" wire, will be about 0.004". This dimension will have a range between 0.003" and 0.005" when the trochar is made from a 0.008" wire.

The shape of the swedged segment of the trochar may also vary. the shape may be oval, circular or even square depending upon the method used to produce the swedged segment. Thus for example the swedged portion of the trochar may be produced by pinching the wire between rollers which are set to have a space between the rollers which is smaller than the diameter of the wire from which the trochar is formed. Alternatively the wire may be extruded with a variable diameter over a short segment of the wire, thus providing a thickened aspect over some distance of the wire.

It is preferred to produce the swedged segment in the wire from which the trochar is formed by striking the wire between symmetrical dies. The surface of the dies are shaped to produce the swedged segment in the wire when the wire is pressed between the dies. In a preferred embodiment, the dies will produce a swedged region which is narrower at one end and increases in width toward the opposite end before quickly ending. The shape of the swedged segment is in this preferred embodiment, spade shaped, with the narrow end of the spade shaped swedged segment closer to the point of the trochar.

Figure 1:
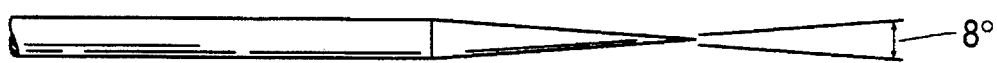
FIG. 1 is a side view of the trochar according to the invention.

The trochar used with the cannula is conically pointed. The interior angle of the point of said trochar, when measured as is illustrated in FIG. 1, may vary between about 35° and 5° depending upon the sharpness of the point desired. A sharp point may be desired if the trochar must pierce a robust or fibrous tissue. For such sharp points, an angle of 8° is preferred and the length of the point of the trochar is about six times the diameter of said trochar. Lengths substantially greater that about six times the diameter of the trochar lead to undesirable delicate points that can flex and break. Therefore, it is preferred that the length of a sharp trochar point is about six times the diameter of the trochar or less.

With respect to the cannulation of small delicate hollow anatomical structures such as a duct or small blood vessel of a subject, or even a major blood vessel of a very small experimental animal, or neonate of any species, the trochar used with the microcannula will have a conical point that is less acute in angle. The trochar point will have an angle in a range between 20° and 35°. Points having an angle between 25° and 30° have been found in practice to be particularly easy to handle when cannulating small blood vessels. A trochar tip angle of about 28° is believed to be preferred.

The trochar may be made of any strong wire stock. It is preferred that the wire is not of a ductile metal since the trochar confers rigidity to the microcannula when it is inserted into the lumen thereof. Furthermore ductile wires cannot be easily inserted into the lumen of the microcannula with the required tight fit without bending or breaking. It is preferred that the trochar is made of stainless steel.

The microcannula of the invention further comprises a segment of the microcannula tube that has an expanded outside diameter and is located distal to the tip of the microcannula. The expanded outside diameter of shoulder 14 may be in the form of a ring of tubing or an "O" ring adhered to the outside wall of the microcannula tube, dried plastic glue or a thickening in the wall of the microcannula itself.

In a preferred embodiment, the expanded outside diameter of the shoulder 14, as indicated above, is provided by a ring of tubing which fits tightly around the outside wall of the microcannula tube 12, but which may be moved if desired to various positions thereon. The advantage gained by a movable ring is that the microcannula may be secured in the cannulated vessel at any desired depth of the tip of the microcannula in the vessel. Thus if a deep cannulation is desired, with the tip of the microcannula advanced far into the cannulated anatomical structure or vessel, the ring forming the shoulder 14 may be moved distally away from the microcannula tip to allow a deep penetration of the microcannula tip prior to securing the microcannula tube 12 with the ligature 20 tied around the vessel 18 on one end and the microcannula tube 12 behind the shoulder 14 as is shown in FIG. 5.

As was mentioned above, the shoulder 14 may be provided by a movable ring in the form of a small piece of tubing. Equally the ring may be an "O" ring or other annular structure. It is preferred that the internal diameter of the tightly fitted movable ring will be sightly smaller that the outside diameter of the hollow tube 12 forming the microcannula. In general the inside diameter of the movable ring and the outside diameter of the microcannula will be chosen so as to establish an interference fit, in which the internal diameter of the movable ring is slightly smaller than the outside diameter of the wall of the tube 12 forming the microcannula. An interference fit in a range of about 0.0015" to 0.0005" will be selected; an interference fit of about 0.001" is preferred.

Figure 5:
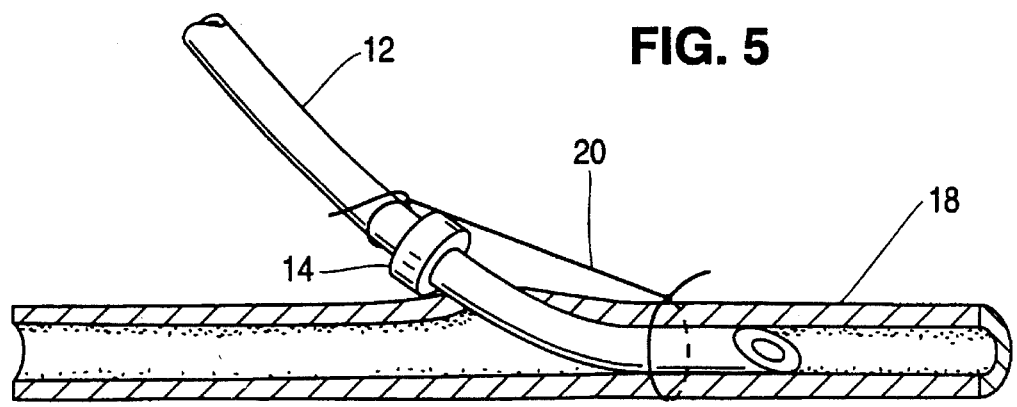
FIG. 5 shows the microcannula in place in a blood vessel or other hollow tube with the blood vessel tied off around the proximal end of the microcannula and the microcannula secured in place.

In general, the movable ring will have an outside diameter large enough to provide a usable stop for securing the ligature 20 as shown in FIG. 5. An outside diameter of at least two to three times the inside diameter of the movable ring is preferred. If the inside diameter of the ring is particularly small, the outside diameter of the ring will be larger than two times the inside diameter. In a preferred embodiment, the tube 12 of the microcannula has an outside diameter of 0.016" and the movable ring has an inside diameter of 0.015" and an outside diameter of 0.043".

It is preferred that the movable ring be made of a material which will stretch sufficiently to allow it to be fitted over the outside wall of the microcannula tube 12; however, if the material comprising the microcannula tube is resilient and may be slightly compressed without substantially closing the lumen of the microcannula tube 12, the movable ring can be made of a more rigid material such as a metal.

When in use, the shoulder 14 is used to secure the distal end of the microcannula using a ligature 20, one end of which is tied around the distal end of the microcannula and the other end of which is tied around the blood vessel 18 surrounding the end of the microcannula proximal to the beveled tip, as depicted in FIG. 5.

The distal end of the microcannula, which is the end of the microcannula away from the beveled tip, may be secured optionally within the lumen of a larger tube which may in turn be secured to the tip of a needle or still larger piece of tubing. The distal end of the microcannula can in this fashion be conveniently connected to conventional fittings for tubing or syringes such as luer lock fittings and the like.

Tubing of the type used to make the microcannula according to the invention can be obtained from suppliers of laboratory wares such as Cole-Parmer, Chicago, Ill. U.S.A.. Wire suitable for the fabrication into the trochar described here in can be obtained from National Standard Company, Santa Fe Springs, Calif., U.S.A.

The present invention further comprises that microcannula described herein above with the trochar described herein above placed in the lumen of the tube forming the microcannula.

When in use to cannulate a small blood vessel or hollow organ the trochar 10 and microcannula 12 are used as a unit. The trochar 10 is placed tightly fitting in the lumen of the microcannula 12 with the trochar tip 11 protruding beyond the microcannula's beveled leading edge 16. The trochar tip 11 is used to pierce the wall of the blood vessel 18. The microcannula's beveled leading edge 16 comes into contact with the outside of the blood vessel 18 outer wall slightly displacing the wall of the blood vessel and stretching the hole punctured in the blood vessel wall. By further advancing the microcannula and trochar together, the microcannula is easily threaded through the hole into the lumen of the blood vessel.

As a result of the tight fit of the trochar and microcannula the cannulation of small blood vessels can be accomplished without the necessity of first incising a blood vessel followed by insertion of a cannula and trochar. By using the trochar and microcannula as a unit, bleeding can be minimized and the possibility of damaging the blood vessel with an incision that is too large is eliminated.

We claim:

1. A microcannula, comprising:

a hollow tube having a cross sectional size smaller than a 24 gauge needle and larger than a 29 gauge needle, said tube having a beveled tip wherein the angle of said bevel is 25°±0.5° and a segment of said tube distal to the tip having an expanded outside diameter; and a solid conically pointed trochar tightly but removably fitted in the lumen of said tube, said trochar sufficiently long to protrude beyond the leading edge of said beveled tip, said trochar having a swedged segment in contact with the inside wall of said tube, said swedged segment being located at a point distal to said conical point and providing sufficient friction against said tube so as to restrict movement of said trochar in said tube.

2. The microcannula of claim 1 wherein said bevel is 25° ± 0.5°.

3. The microcannula of claim 1 wherein the outside diameter of said tube is about 0.016 inch.

4. The microcannula of claim 1 wherein the outside diameter of said tube is about 0.016 inch ± 0.001 inch.

5. The microcannula of claim 1 wherein the inside diameter of said tube is about 0.008 inch.

6. The microcannula of claim 1 wherein the inside diameter of said tube is about 0.008 inch ± 0.001 inch.

7. The microcannula of claim 1 wherein the walls of said tube are a biocompatible polymer.

8. The microcannula of claim 1 wherein the point of said trochar forms an angle in a range from 5° to 35°.

9. The microcannula of claim 8 wherein the point of said trochar forms an angle of about 8° +/− 3°.

10. The microcannula of claim 8 wherein the point of said trochar forms an angle in a range from 20° to 35°.

11. The microcannula of claim 8 wherein the point of said trochar forms an angle in a range from 25° to 30°.

12. The microcannula of claim 8 wherein the point of said trochar forms an angle of about 28°.

13. The microcannula of claim 1 wherein the expanded outside diameter of said segment is provided by a ring around the outside of said tube.

14. The microcannula of claim 13 wherein said ring is tightly fitted on said tube but may be moved thereon.

15. The microcannula of claim 14 wherein said ring and the outside of said tube are in an interference fit with respect to one another.

16. The microcannula of claim 1 wherein the outside diameter of said trochar is slightly smaller than the inside diameter of said tube, said trochar having a swedged segment in contact with the inside wall of said tube.

17. The microcannula of claim 16 wherein said swedged segment is spade shaped and the narrow portion of said spade shaped swedged segment is closest to the tip of said trochar.

* * * * *